(12) United States Patent
Wu et al.

(10) Patent No.: US 9,120,738 B2
(45) Date of Patent: Sep. 1, 2015

(54) CRYSTALLINE FORMS OF BIMATOPROST ACID, METHODS FOR PREPARATION, AND METHODS FOR USE THEREOF

(71) Applicant: ALLERGAN, INC., Irvine, CA (US)

(72) Inventors: Ke Wu, Irvine, CA (US); Shaoxin Feng, Tustin, CA (US); Thomas K. Karami, Aliso Viejo, CA (US); Scott W. Smith, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/136,914

(22) Filed: Dec. 20, 2013

(65) Prior Publication Data

US 2014/0187636 A1 Jul. 3, 2014

Related U.S. Application Data

(60) Provisional application No. 61/746,708, filed on Dec. 28, 2012.

(51) Int. Cl.
C07C 59/54 (2006.01)

(52) U.S. Cl.
CPC ............. C07C 59/54 (2013.01); *C07B 2200/13* (2013.01)

(58) Field of Classification Search
USPC .......................................... 514/570; 562/471
See application file for complete search history.

(56) References Cited

U.S. PATENT DOCUMENTS 7,851,504 B2 * 12/2010 Chang et al. .................. 514/530
2011/0152376 A1 * 6/2011 Ambrus et al. ............... 514/622

FOREIGN PATENT DOCUMENTS

WO 90-02553 3/1990
WO 2012-164324 6/2012

OTHER PUBLICATIONS

Caira, Mino, Crystalline Polymorphism of Organic Compounds, Topics in Current Chemistry, Jan. 1998, 163-208, 198.
Lee, Anne et al, Clinical Utility and Differential Effects of Prostaglandin Analogs in the Management of Raised Intraocular Pressure and Ocular Hypertension, Clinical Ophthalmology, Jan. 2010, 741-764, 4.
International Searching Authority, Notification of Transmittal of the International Search Report and Written Opinion of the International Searching Authority, or the Declaration, Date of Mailing: Feb. 19, 2014, International Patent Application No. PCT/US2013/078334, filed Dec. 30, 2013.

\* cited by examiner

*Primary Examiner* — Kathrien Cruz
(74) *Attorney, Agent, or Firm* — Jonathan Y. Bass

(57) ABSTRACT

The invention provides new crystalline forms of 7-[3,5-Dihydroxy-2-(3-hydroxy-5-phenyl-pent-1-enyl)-cyclopentyl]-hept-5-enoic acid. This compound is commonly referred to as "bimatoprost acid." The novel crystalline forms are designated forms I, II, and III. The invention crystalline forms are useful for solid ocular implant formulations, utilized in the treatment of various ocular conditions, such as, for example, ocular hypertension. In addition, invention crystalline forms are useful for solid or semisolid dosage formulations used to treat ocular hypertension.

17 Claims, 10 Drawing Sheets

Figure 2: IR spectra of Bimatoprost Acid Polymorph I (lower spectrum) and Polymorph II (upper spectrum).

Figure 3: MDSC Thermographs of Polymorph I (upper curve) and Polymorph II (lower curve).

Figure 4: Equilibrium Solubility of Polymorphs I & II in Anisole at 6°C and 25°C.

Figure 5: Calculated Transition Temperature between the Enantiotropic Polymorphs I and II by using the Equilibrium Solubility and MDSC Data. The Estimated Transition Temperature is 56.7°C ± 1.7°C.

Figure 6: Formation of Polymorph III upon Exposure of Polymorph I to Moisture by VSA Figure 7: Formation of Polymorph III upon Exposure of Polymorph II to Moisture by VSA, Polymorph III Forms at 2$^{nd}$ Adsorption Cycle at RH ≥ 75%

Figure 8: MDSC analysis of Polymorph III of Bimatoprost Acid

Schematic Workflow of the Experiments on Bimatoprost Acid.

FIG 10: Summary of the Results

| # | Solvent | Method of Preparation | Final Product |
|---|---|---|---|
| 1 | diethyl | RT slurrying and subsequent maturation | Form 2 |
| 2 | DCM | Vacuum drying after antisolvent (heptane) addition | Mixture of Form 1 and 2 |
| 3 | acetone | n/a | yellow oil |
| 4 | methanol | n/a | yellow oil |
| 5 | THF | n/a | yellow oil |
| 6 | EtOAc | antisolvent (heptane) addition and maturation | Form 1 |
| 7 | ethanol | n/a | yellow oil |
| 8 | acetonitril | n/a | yellow oil |
| 9 | IPA | n/a | yellow oil |
| 11 | water | n/a | yellow oil |
| 12 | NitroMe | n/a | yellow oil |
| 13 | 1,4- | n/a | yellow oil |
| 15 | Anisole | Vacuum drying after antisolvent (toluene) addition | Form 1 |
| 18 | DMF | n/a | yellow oil |
| 19 | MEK | Vacuum drying after antisolvent (heptane) addition | Mixture, majorly Form 1 |
| 21 | Cumene | Maturation and 5°C cooling | Form 1 |
| 23 | Ethylene | n/a | yellow oil |
| 24 | NMP | n/a | yellow oil |

CRYSTALLINE FORMS OF BIMATOPROST ACID, METHODS FOR PREPARATION, AND METHODS FOR USE THEREOF

CROSS REFERENCE TO RELATED APPLICATION

This application claims the benefit of U.S. Provisional Application Ser. No. 61/746,708, filed Dec. 28, 2012, the disclosure of which is hereby incorporated in its entirety herein by reference.

FIELD OF THE INVENTION

The present invention relates generally to crystalline forms of bimatoprost acid and particularly to newly identified crystalline forms of bimatoprost acid. The present invention further relates to methods for its preparation and to methods for treating various disorders associated with ocular hypertension, hair growth and fat reduction.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. Exp. Eye Res. 1971, 11, pp. 170-177; Bito, L. Z. Biological Protection with Prostaglandins Cohen, M. M., ed., Boca Raton, Fla. CRC Press Inc., 1985, pp. 231-252; and Bito, L. Z., Applied Pharmacology in the Medical Treatment of Glaucomas Drance, S. M. and Neufeld, A. H. eds., New York, Grune & Stratton, 1984, pp. 477-505). Such prostaglandins include $PGF_{2\alpha}$, $PGF_{1\alpha}$ $PGE_2$, and certain lipid-soluble esters, such as $C_1$ to $C_5$ alkyl esters, e.g. 1-isopropyl ester, of such compounds. Other uses of bimatoprost includes use in hair growth including scalp hair, eyelashes, and eyebrows. Bimatoprost has also shown promise in localized fat reduction and inhibition of adipocyte differentiation.

It is known however that many drug compounds exist in two or more crystalline forms, referred to as polymorphs. These polymorphs of the same molecule exhibit different physical properties, such as melting point, solubility, hardness, etc. In such cases, the danger exists of less soluble polymorphic forms precipitating from a solution made from another more soluble but less stable form. The formation of crystals in an ophthalmic solution can cause serious injury to the eye. In addition, precipitation of the drug substance may cause an apparent reduction in potency and bioavailability of the product. The following references are incorporated by references in their entireties: U.S. Pat. Nos. 5,688,819; 6,403,649; 7,751,504 and A. Burger, R. Ramberger, "On the polymorphism of pharmaceuticals and other molecular crystals. I. Theory of thermodynamic rules", Mikrochimica Acta (1979), 2(3-4), 259-71.

SUMMARY OF THE INVENTION

The present invention provides new crystalline forms of 7-[3,5-Dihydroxy-2-(3-hydroxy-5-phenyl-pent-1-enyl)-cyclopentyl]-hept-5-enoic acid. This compound is commonly referred to as "bimatoprost acid." The novel crystalline forms of the present invention are designated forms I, II, and III. The invention crystalline forms are useful for solid ocular implant formulations, utilized in the treatment of various ocular conditions, such as, for example, ocular hypertension. In addition, invention crystalline forms are useful for solid or semi-solid dosage formulations used to treat ocular hypertension.

In another embodiment of the invention, there provided pharmaceutical compositions including a therapeutically effective amount of 7-[3,5-Dihydroxy-2-(3-hydroxy-5-phenyl-pent-1-enyl)-cyclopentyl]-hept-5-enoic acid in crystalline forms I, II, or III in an ophthalmically acceptable carrier therefore such as an ophthalmic topical solution.

In another embodiment, there provided methods for treating ocular hypertension. Such methods can be performed, for example, by administering to a subject in need thereof a therapeutically effective amount of 7-[3,5-Dihydroxy-2-(3-hydroxy-5-phenyl-pent-1-enyl)-cyclopentyl]-hept-5-enoic acid in crystalline forms I, II, or III in an ophthalmically acceptable carrier, that does not affect the structure of the crystalline forms.

In another embodiment, there provided methods for treating glaucoma. Such methods can be performed, for example, by administering to a subject in need thereof a therapeutically effective amount of 7-[3,5-Dihydroxy-2-(3-hydroxy-5-phenyl-pent-1-enyl)-cyclopentyl]-hept-5-enoic acid in crystalline forms I, II, or III in an ophthalmically acceptable carrier such as a topical solution, or in an ocular implant. XRPD analysis has shown that the crystalline form of other bimatoprost polymorphs forms convert to an amorphous material after hot melt extrusion (typically at ca. 60-70° C.). The existing crystalline form (Form 1) has a melting endotherm peaked at 66.4° C., which is within the vicinity of the extrusion temperature making it useful for an ocular implant.

Some embodiments of the present invention include:
1. 7-[3,5-Dihydroxy-2-(3-hydroxy-5-phenyl-pent-1-enyl)-cyclopentyl]-hept-5-enoic acid in crystalline form I.
2. 7-[3,5-Dihydroxy-2-(3-hydroxy-5-phenyl-pent-1-enyl)-cyclopentyl]-hept-5-enoic acid in crystalline form II.
3. 7-[3,5-Dihydroxy-2-(3-hydroxy-5-phenyl-pent-1-enyl)-cyclopentyl]-hept-5-enoic acid in crystalline form III.
4. The crystalline form of paragraph 1 having the X-ray diffraction pattern substantially as shown in FIG. 1 and the peak data as shown in Table 1 as to polymorph I.
5. The crystalline form of paragraph 2 having the X-ray diffraction pattern substantially as shown in FIG. 1 and the peak data as shown in Table 1 as to polymorph II.
6. The crystalline form of paragraph 3 having the X-ray diffraction pattern substantially as shown in FIG. 1 and the peak data as shown in Table 1 as to polymorph III.
7. The crystalline form of paragraph 1 having a melting endotherm onset at about 63.2° C. and a fusion enthalpy of about 65.6 J/g.
8. The crystalline form of paragraph 2 having a melting endotherm onset at about 62.2° C. and a fusion enthalpy of about 81.5 J/g.
9. The crystalline form of paragraph 1 having the MDSC profile as shown in FIG. 3.
10. The crystalline form of paragraph 2 having the MDSC profile as shown in FIG. 3.
11. The crystalline form of paragraph 3 having the MDSC profile as shown in FIG. 8.
12. A pharmaceutical composition comprising a therapeutically effective amount of 7-[3,5-Dihydroxy-2-(3-hydroxy-5-phenyl-pent-1-enyl)-cyclopentyl]-hept-5-enoic acid in crystalline form I in an ophthalmically acceptable carrier.
13. A pharmaceutical composition comprising a therapeutically effective amount of 7-[3,5-Dihydroxy-2-(3-hydroxy-5-phenyl-pent-1-enyl)-cyclopentyl]-hept-5-enoic acid in crystalline form II in an ophthalmically acceptable carrier.
14. A pharmaceutical composition comprising a therapeutically effective amount of 7-[3,5-Dihydroxy-2-(3-hydroxy-5-phenyl-pent-1-enyl)-cyclopentyl]-hept-5-enoic acid in crystalline form III in an ophthalmically acceptable carrier.
15. A method for treating ocular hypertension comprising administering to a subject in need thereof a therapeutically effective amount of 7-[3,5-Dihydroxy-2-(3-hydroxy-5-phenyl-pent-1-enyl)-cyclopentyl]-hept-5-enoic acid in crystalline form I in an ophthalmically acceptable carrier.
16. A method for treating ocular hypertension comprising administering to a subject in need thereof a therapeutically effective amount of 7-[3,5-Dihydroxy-2-(3-hydroxy-5-phenyl-pent-1-enyl)-cyclopentyl]-hept-5-enoic acid in crystalline form II in an ophthalmically acceptable carrier.
17. A method for treating ocular hypertension comprising administering to a subject in need thereof a therapeutically effective amount of 7-[3,5-Dihydroxy-2-(3-hydroxy-5-phenyl-pent-1-enyl)-cyclopentyl]-hept-5-enoic acid in crystalline form III in an ophthalmically acceptable carrier.
18. The method of paragraph 15 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.
19. The method of paragraph 16 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.
20. The method of paragraph 17 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.
21. The compositions of paragraphs 12, 13 and 14 wherein the pharmaceutical composition is a topical ophthalmic solution to be dosed at least once a day or more.
22. The compositions of paragraphs 12, 13 and 14 wherein the pharmaceutical composition is a topical ophthalmic emulsion to be dosed at least once a day or more.
23. The composition of paragraphs 12, 13 and 14 wherein the pharmaceutical composition is an ocular implant.
24. The composition of paragraphs 12, 13, 14, 21, 22 and 23 wherein the concentration of the active is selected from 0.01, 0.02, 0.03, 0.04. 0.05, 0.06, 0.07, 0.08, 0.09, 0.1, 0.2, 0.3, 0.4. 0.5, 0.6, 0.7, 0.8, 0.9 to 1.0% w/v.
25. The composition of paragraph 24 wherein the composition is used to promote hair growth or localized fat reduction.

BRIEF DESCRIPTION OF THE DRAWINGS

FIG. 10 summarizes the results of the experiments.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

It is to be understood that "7-[3,5-Dihydroxy-2-(3-hydroxy-5-phenyl-pent-1-enyl)-cyclopentyl]-hept-5-enoic acid" and "bimatoprost acid" refer to the same compound and may be used interchangeably throughout.

In addition, "crystalline form" and "polymorphic form" may be used interchangeably throughout the specification. "Crystalline form I" or "form I", "crystalline form II" or "form II", "crystalline form III" or "form III" may also be referred to as "polymorph I", "polymorph II", or "polymorph III".

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

Figure 9:
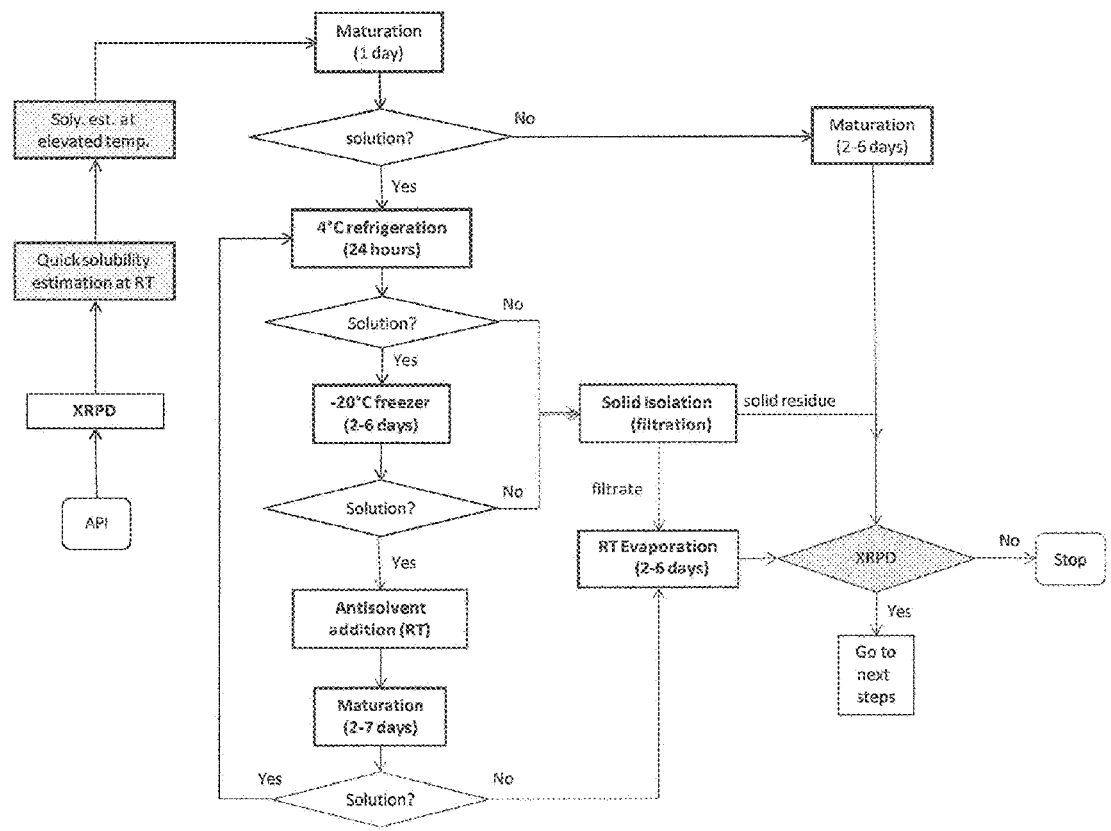
FIG. 9 shows schematic workflow of the experiments on Bimatoprost Acid.

Crystallization Process:

Bimatoprost acid was manufactured by Organic Consultants, Inc. The purity of the compound per CoA was 100% determined by HPLC. FIGS. 9 and 10 summarize the crystallization processs.

Instrumentation:

XRPD Characterization

1. The following XRPD condition was used:
Equipment: Rigaku Miniflex;
Scan range: 5-45° (2θ);
Scan speed: 2° (2θ) per minute; and,
Step width: 0.05° (2θ)
Cu Kα, λ=1.54 Å, 30 kV
Samples isolated from the experiments were immediately analyzed and the same sample was rescanned after overnight vacuum drying at 35° C. Approximately 3-5 mg of the samples were gently pressed on zero background sample holders and subjected to XRPD scan.

MDSC Analysis:

The following method was used for thermal analysis by MDSC:
Equipment: TA DSC Q2000;
Scan range: 20-122° C.;
Heating rate: 1° C. per minute;
Modulation period: 60 seconds;
Modulation amplitude: 0.159° C.;
Approximately 2-3 mg of the sample was placed in T-zero nonhermetic pan and subjected to MDSC heating ramp.

The present invention provides bimatoprost acid in new polymorphic forms, designated as polymorphs I, II, and III. Physical characterization of bimatoprost acid led to the discovery of these three polymorphs. The results of a polymorph screening study of bimatoprost acid showed that polymorph II forms when polymorph I is maturated in diethyl ether upon thermo-cycling at 12-32° C. XRPD patterns of polymorph I, polymorph II and polymorph III are presented in FIG. 1.

Figure 2:
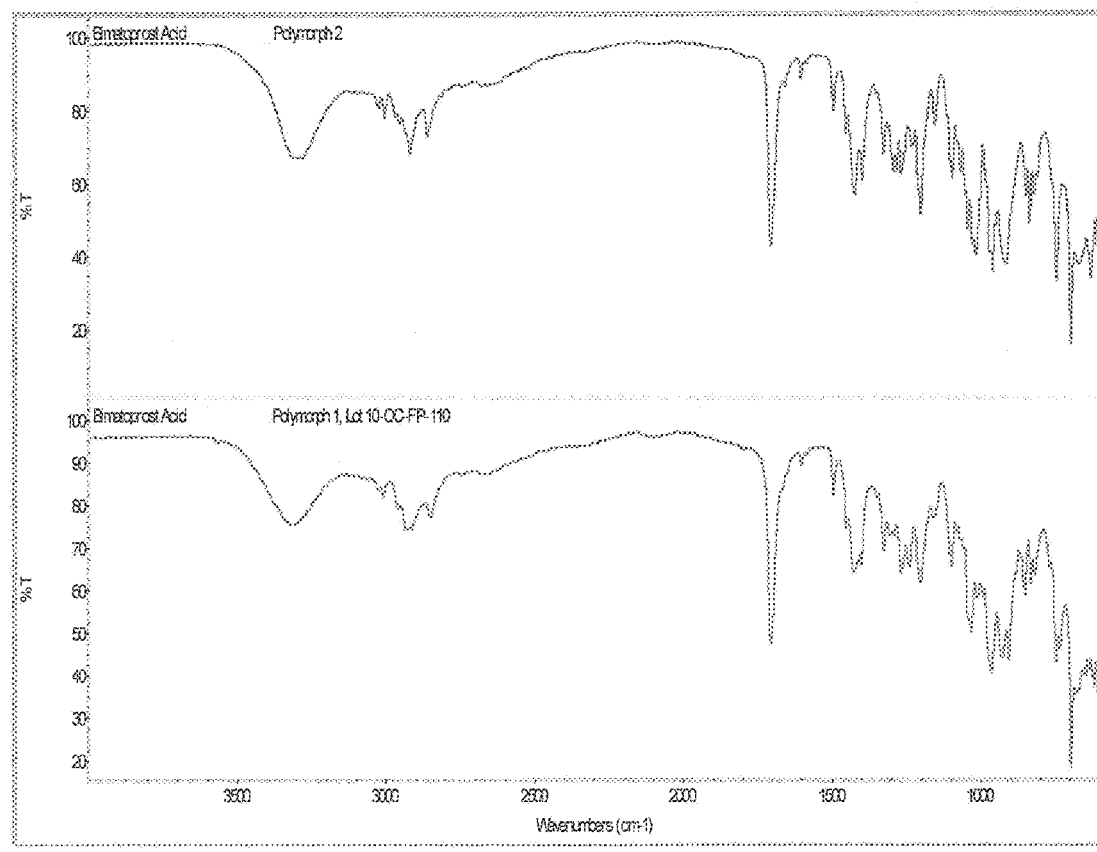
FIG. 2 shows IR spectra of Bimatoprost Acid Polymorph I (lower spectrum) and Polymorph II.
Figure 3:
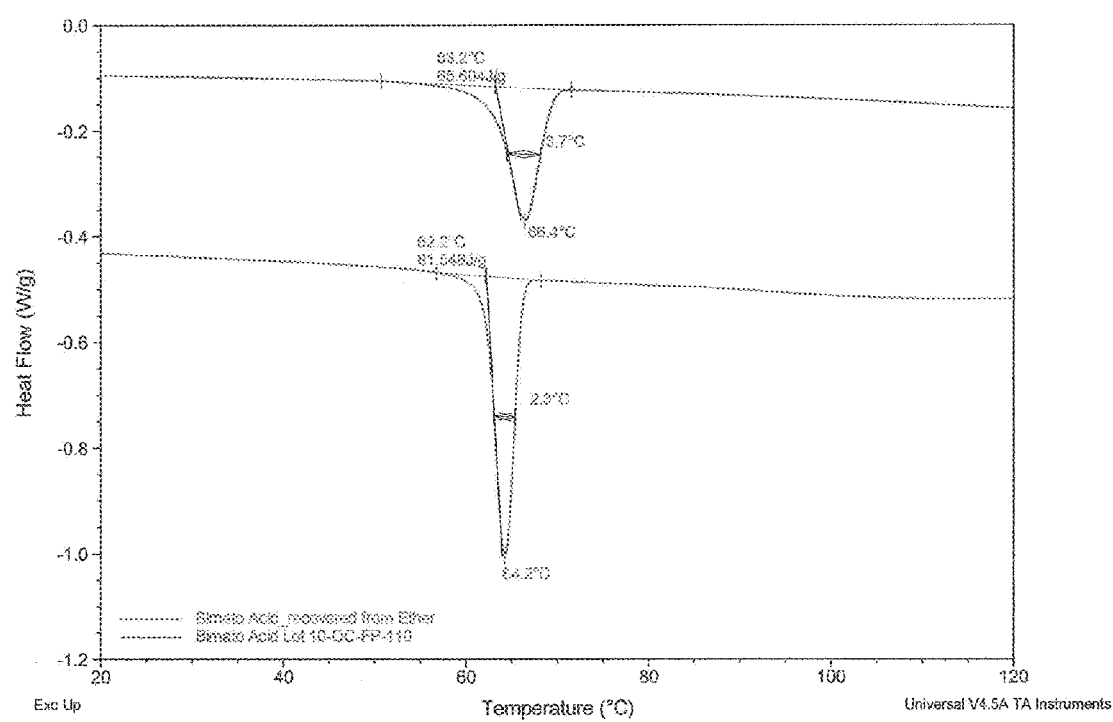
FIG. 3 shows the MDSC Thermographs of Polymorph I and Polymorph II.

FIG. 2 shows that the FTIR spectra of polymorphs I and II are identical indicating that they have the same chemical composition. The XRPD and FTIR data indicate the two forms are polymorphic and not different chemical entities. Polymorph I and polymorph II have an enantiotropic polymorphic relationship. Enantiotropic polymorphs are characterized by a difference in melting points and fusion enthalpies, where the higher melting polymorph has a lower fusion enthalpy. Modulated differential calorimetric (MDSC) data in FIG. 3 shows that polymorph I has a melting endotherm onset (T onset) at 63.2° C. and a fusion enthalpy ($\Delta H_f$) of 65.6 J/g as compared to the corresponding properties for polymorph II (62.2° C. and 81.5 J/g, respectively).

The differences in free energy between the polymorphs were measured as a function of temperature in order to determine the transition temperature and relative stability versus temperature. Isothermal competitive co-slurries of polymorph I and II (1:1 ratio at 5, 20 and 35° C.) showed that polymorph I converts to polymorph II at all three temperatures, indicating that polymorph II is the more stable form over the temperature range of 5-35° C.

Figure 4:
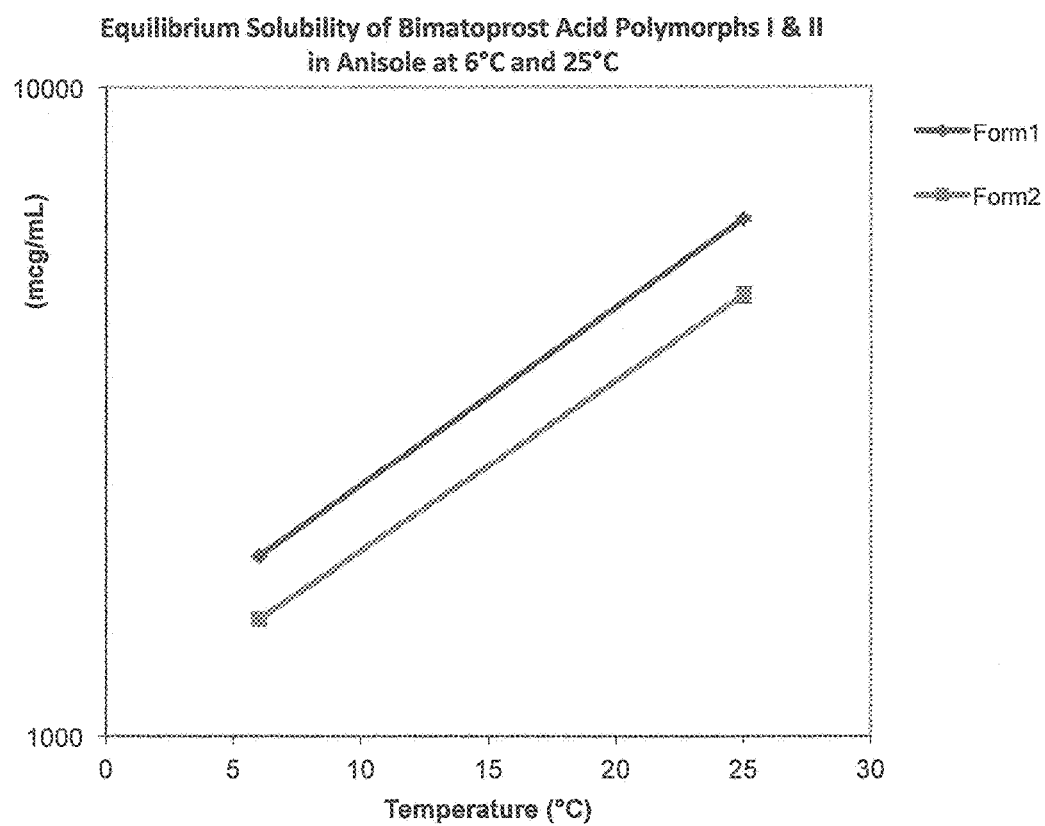
FIG. 4 shows the Equilibrium Solubility of Polymorphs I & II in Anisole.
Figure 5:
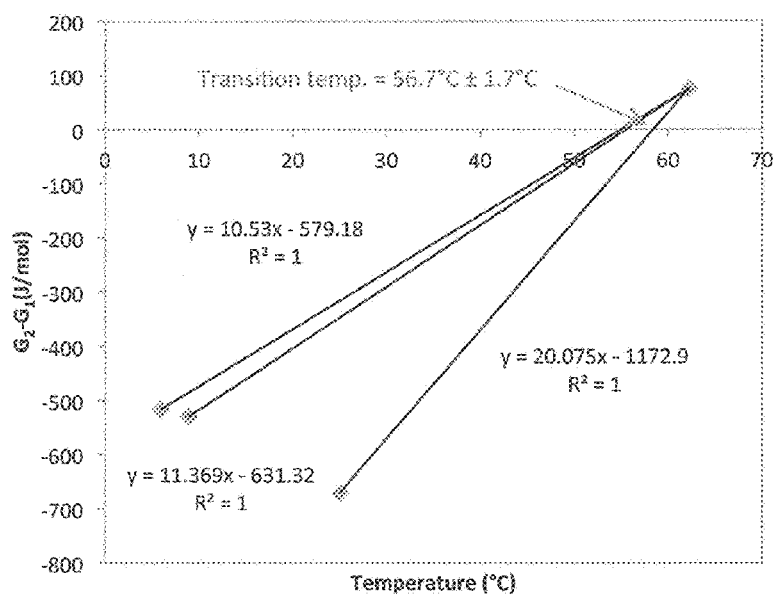
FIG. 5 shows the Transition Temperature between the Enantiotropic Polymorphs I and II to moisture by VSA.

FIG. 4 shows the thermodynamic equilibrium solubility of the anhydrous polymorphs in anisole at 6° C. and 25° C. At both temperatures polymorph II has the lower solubility indicating that polymorph II is the lower energy form at temperature 6-25° C. Anisole was selected as solvent based on good stability and measurable solubility of bimatoprost acid polymorphs in the studied temperature range. Solubility studies could not be performed at temperatures above 40° C. in order to determine the enantiotropic polymorph transition temperature because bimatoprost acid transforms to an oil in anisole. Another solvent, nitromethane, was selected to detect the solubility of bimatoprost acid at 9 and 22° C. At 9° C., the solubility of polymorph I (4.1±0.3 mg/mL) is significantly higher than the solubility of polymorph II (3.3±0.2 mg/mL) which suggests the polymorph II is more stable than polymorph I at 9° C. At 22° C., both forms converted to oils where no comparison between the two polymorphs could be made.

Figure 6:
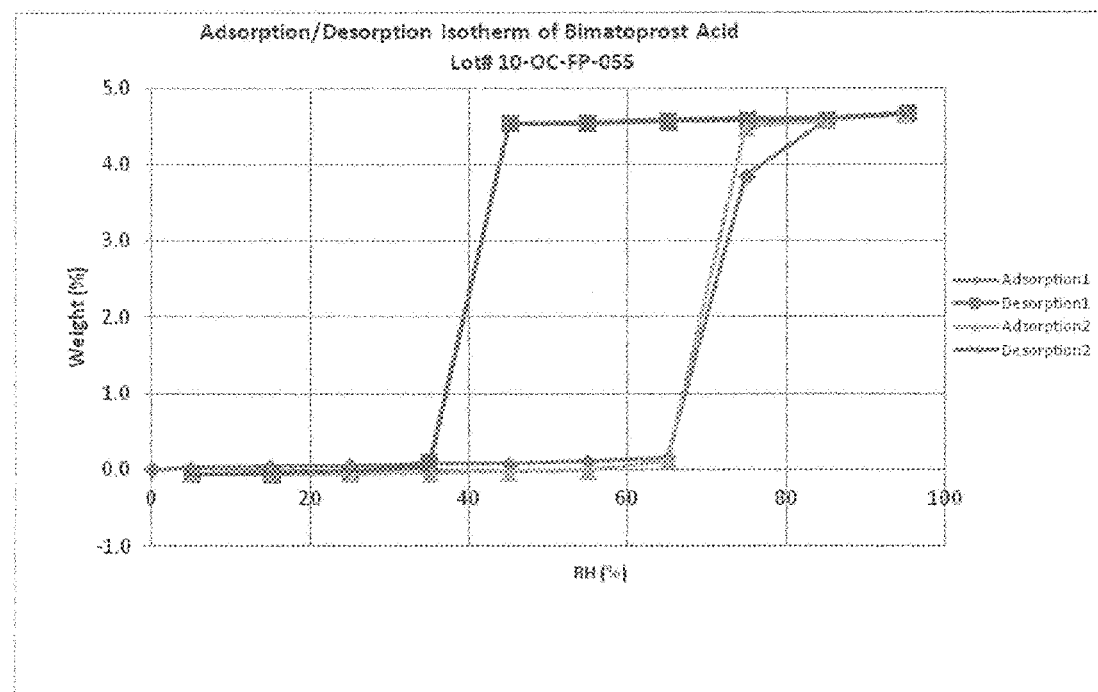
FIG. 6 shows the Formation of Polymorph III upon Exposure of Polymorph I.
Figure 7:
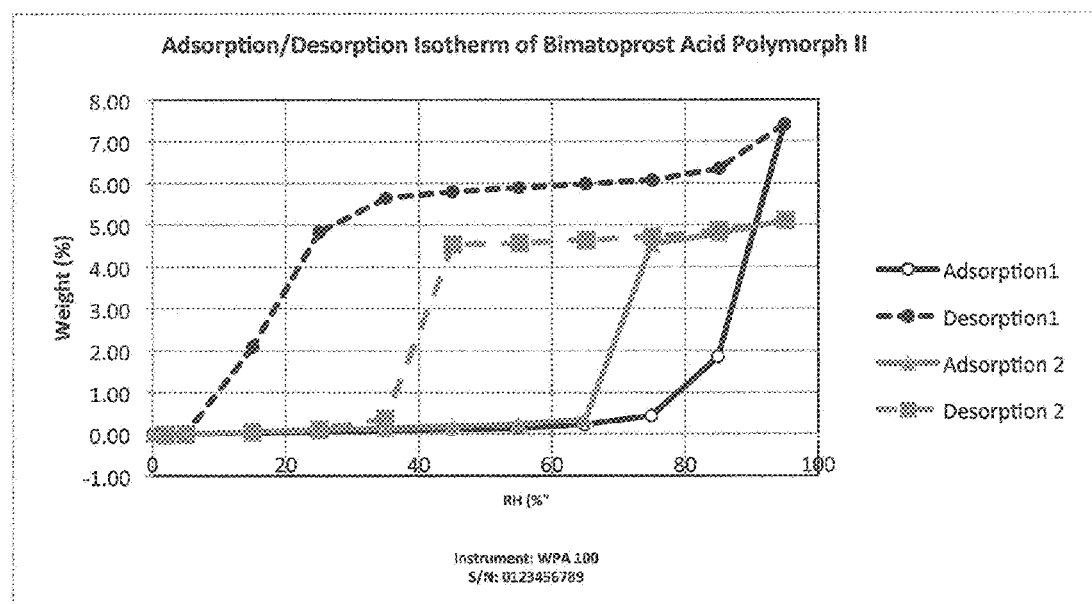
FIG. 7 shows the Formation of Polymorph III upon Exposure of Polymorph II to Moisture by VSA.

The crystalline monohydrate form (designated polymorph III) was discovered upon vapor sorption analysis (VSA) of both polymorph I and polymorph II. FIG. 6 shows that at RH~75% polymorph I absorbs 4.42 w/w % water, which is equivalent to a stoichiometric monohydrate. The conversion of polymorph I to the monohydrate form was confirmed by XRPD. The generated monohydrate converted beck to the initial polymorph 1 upon drying in vapor sorption analyzer at 25° C. Vapor sorption analysis also showed that polymorph II converts to a hydrated form at water activity above 85% RH. The $2^{nd}$ adsorption cycle of polymorph II reconfirms formation of the monohydrate again at RH~75% (FIG. 7). At 25° C., the relative humidity at which polymorph II forms the monohydrate is greater than that for polymorph I, consistent with the assertion that polymorph II is the more stable form at 25° C. The thermal analysis (MDSC) of the monohydrate form indicates a melting endotherm onset ($T_{onset}$) at 53.9° C. and a fusion enthalpy ($\Delta H_f$) of 72.4 J/g for the monohydrate form (see FIG. 8).

Pharmaceutical compositions may be prepared by combining a therapeutically effective amount of polymorphs I, II, or III of bimatoprost acid according to the invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations or preferably about 0.01-to about 0.1% w/v and 0.01% w/v to about 0.03% w/v. An "effective amount" is an amount sufficient to accomplish a stated purpose (e.g., achieve the effect for which it is administered, treat a disease, reduce one or more symptoms of a disease or condition). An example of an "effective amount" is an amount sufficient to contribute to the treatment, prevention, or reduction of a symptom or symptoms of a disease, which can be referred to as a "therapeutically effective amount." A "reduction" of a symptom or symptoms (and grammatical equivalents of this phrase) means decreasing of the severity or frequency of the symptom(s), or elimination of the symptom(s). The actual amount effective for a particular application will depend, inter alia, on the condition being treated. "Treatment", "treat" or "treating" can refer to curing any disease or condition or reducing or alleviating the symptoms of the disease or condition For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

Ingredient Amount (% w/w) active ingredient about 0.001-5 preservative 0-0.10 vehicle 0-40 tonicity adjustor 0-10 buffer 0.01-10 pH adjustor q.s. pH 4.5-7.5 antioxidant as needed surfactant as needed purified water as needed to make 100%.

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 ml.

Table 1 shows characteristic peaks of polymorphic forms I, II and III of bimatoprost acid.

TABLE 1

Characteristic XRPD Peaks (Cu K) for Polymorphic Forms of Bimatoprost Acid

| Bimatoprost Acid | Polymorph I | Polymorph II | Polymorph III |
|---|---|---|---|
| Characteristic XRPD Peaks (2-theta) | 13.5, 14.9, 16.3, 17.1, 18.0, 18.4, 19.1, 19.9, 23.8, 24.9, 26.5 | 12.0, 14.2, 16.0, 18.8, 20.6, 22.6, 24.1, 28.1, 35.9, 36.5 | 3.9, 9.8, 13.0, 14.5, 15.4, 18.4, 19.3, 19.7, 20.8, 24.6 |

While this invention has been described with respect to these specific examples, it is understood that other modifications and variations are possible without departing from the spirit of the invention.

Figure 1:
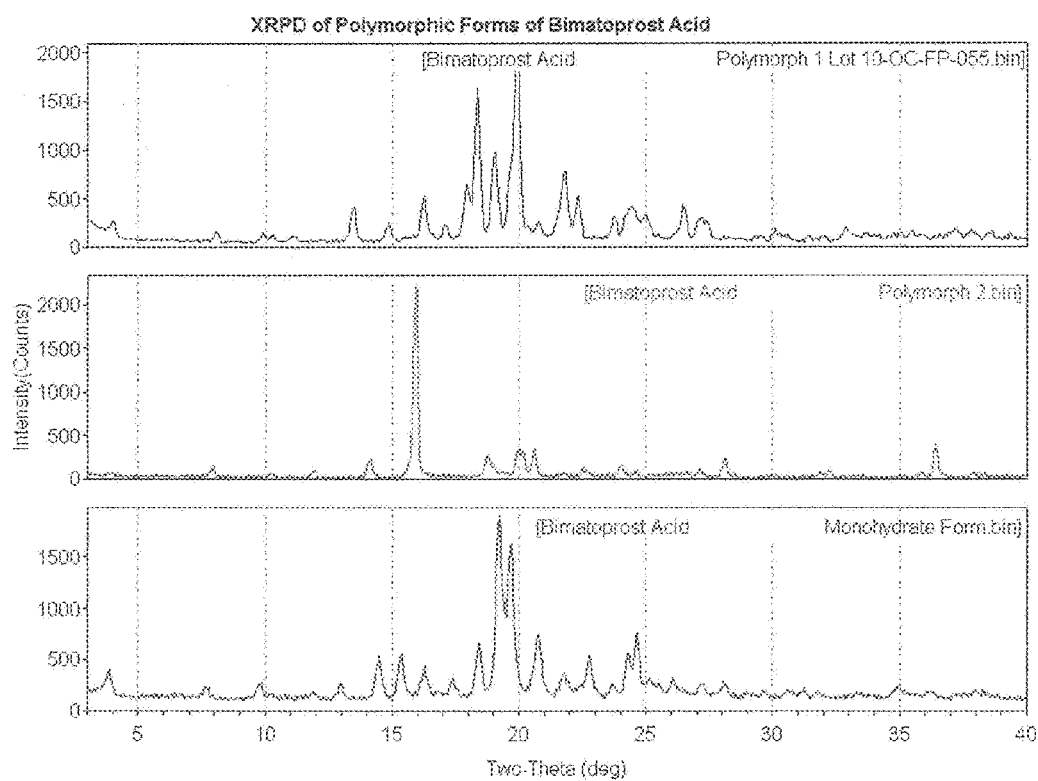
FIG. 1 shows XRPD Patterns of Polymorphic Forms I, II and III of Bimatoprost Acid.

What is claimed is:

1. 7-[3,5-Dihydroxy-2-(3-hydroxy-5-phenyl-pent-1-enyl)-cyclopentyl]-hept-5-enoic acid in crystalline form I as characterized by X-ray diffraction pattern of about 13.5, 14.9, 16.3, 17.1, 18.0, 18.4, 19.1, 19.9, 23.8, 24.9, 26.5, and having the X-ray diffraction pattern substantially as shown in FIG. 1.

2. 7-[3,5-Dihydroxy-2-(3-hydroxy-5-phenyl-pent-1-enyl)-cyclopentyl]-hept-5-enoic acid in crystalline form II as characterized by X-ray diffraction pattern of about, 12.0, 14.2, 16.0, 18.8, 20.6, 22.6, 24.1, 28.1, 35.9, 36.5 and having the X-ray diffraction pattern substantially as shown in FIG. 1.

3. 7-[3,5-Dihydroxy-2-(3-hydroxy-5-phenyl-pent-1-enyl)-cyclopentyl]-hept-5-enoic acid in crystalline form III as characterized by X-ray diffraction pattern of about 3.9, 9.8, 13.0, 14.5, 15.4, 18.4, 19.3, 19.7, 20.8, 24.6.

4. The crystalline form of claim 1 having a melting endotherm onset at about 63.2° C. and a fusion enthalpy of about 65.6 J/g.

5. The crystalline form of claim 2 having a melting endotherm onset at about 62.2° C. and a fusion enthalpy of about 81.5 J/g.

6. The Modulated Differential Calorimetric crystalline form of claim 1 having the profile as shown in FIG. 3.

7. The Modulated Differential Calorimetric crystalline form of claim 2 having the profile as shown in FIG. 3.

Figure 8:
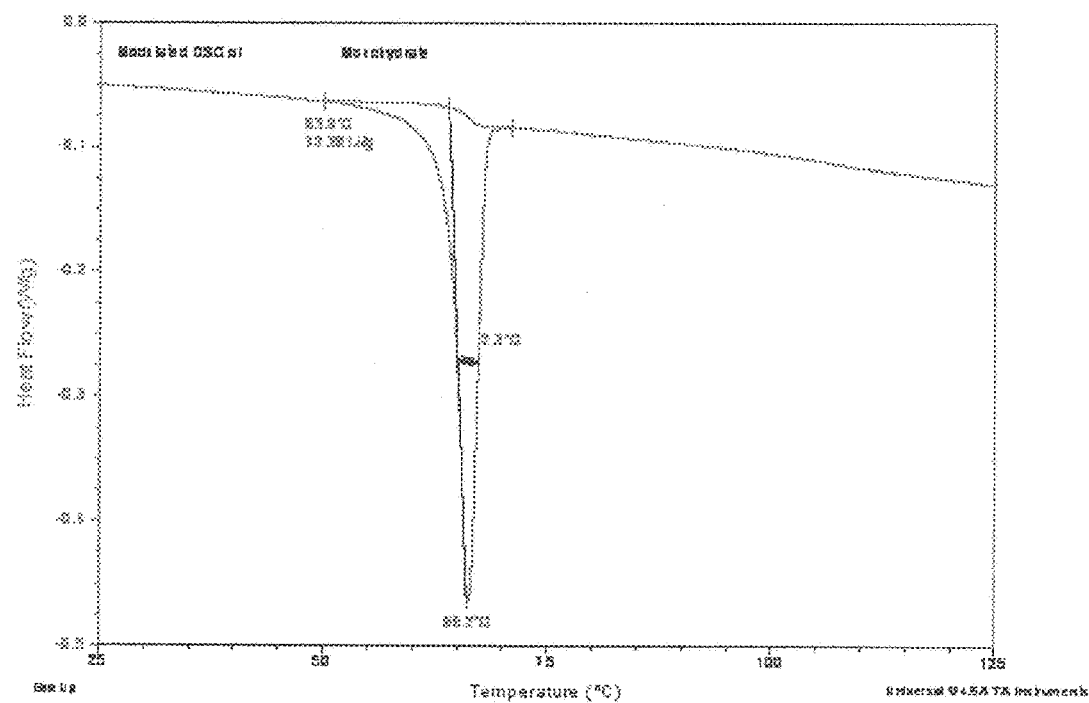
FIG. 8 shows an MDSC Thermograph of Polymorph III.

8. The Modulated Differential Calorimetric crystalline form of claim 3 having the profile as shown in FIG. 8.

9. A pharmaceutical composition comprising a therapeutically effective amount of 7-[3,5-Dihydroxy-2-(3-hydroxy-5-phenyl-pent-1-enyl)-cyclopentyl]-hept-5-enoic acid in crystalline form I in an ophthalmically acceptable carrier.

10. A pharmaceutical composition comprising a therapeutically effective amount of 7-[3,5-Dihydroxy-2-(3-hydroxy-5-phenyl-pent-1-enyl)-cyclopentyl]-hept-5-enoic acid in crystalline form II in an ophthalmically acceptable carrier.

11. A pharmaceutical composition comprising a therapeutically effective amount of 7-[3,5-Dihydroxy-2-(3-hydroxy-5-phenyl-pent-1-enyl)-cyclopentyl]-hept-5-enoic acid in crystalline form III in an ophthalmically acceptable carrier.

12. A method for treating ocular hypertension comprising administering to a subject in need thereof a therapeutically effective amount of 7-[3,5-Dihydroxy-2-(3-hydroxy-5-phenyl-pent-1-enyl)-cyclopentyl]-hept-5-enoic acid in crystalline form I in an ophthalmically acceptable carrier.

13. A method for treating ocular hypertension comprising administering to a subject in need thereof a therapeutically effective amount of 7-[3,5-Dihydroxy-2-(3-hydroxy-5-phenyl-pent-1-enyl)-cyclopentyl]-hept-5-enoic acid in crystalline form II in an ophthalmically acceptable carrier.

14. A method for treating ocular hypertension comprising administering to a subject in need thereof a therapeutically effective amount of 7-[3,5-Dihydroxy-2-(3-hydroxy-5-phenyl-pent-1-enyl)-cyclopentyl]-hept-5-enoic acid in crystalline form III in an ophthalmically acceptable carrier.

15. The method of claim 12 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.

16. The method of claim 13 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.

17. The method of claim 14 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.

* * * * *

UNITED STATES PATENT AND TRADEMARK OFFICE
CERTIFICATE OF CORRECTION

Page 1 of 1

PATENT NO. : 9,120,738 B2
APPLICATION NO. : 14/136914
DATED : September 1, 2015
INVENTOR(S) : Ke Wu et al.

It is certified that error appears in the above-identified patent and that said Letters Patent is hereby corrected as shown below:

In the Drawings

On Sheet 10 of 10, in FIG. 10, line 10, delete "acetonitril" and insert -- acetonitrile --, therefor.

In the Specification

In column 5, line 8, delete "meaning" and insert -- meaning. --, therefor.

In column 5, line 15, delete "processs." and insert -- process. --, therefor.

In column 6, line 46, delete "0.01-to" and insert -- 0.01 to --, therefor.

In column 6, lines 61-62, delete "condition" and insert -- condition. --, therefor.

In the Claims

In column 8, line 13, in Claim 2, delete "about," and insert -- about --, therefor.

In column 8, line 26, in Claim 6, after "The", delete "Modulated Differential Calorimetric".

In column 8, line 27, in Claim 6, after "the" insert -- Modulated Differential Calorimetric --.

In column 8, line 28, in Claim 7, after "The", delete "Modulated Differential Calorimetric".

In column 8, line 29, in Claim 7, after "the" insert -- Modulated Differential Calorimetric --.

In column 8, line 30, in Claim 8, after "The", delete "Modulated Differential Calorimetric".

In column 8, line 31, in Claim 8, after "the" insert -- Modulated Differential Calorimetric --.

Signed and Sealed this
Twenty-ninth Day of March, 2016

Michelle K. Lee
*Director of the United States Patent and Trademark Office*